US00PP11995P2

(12) United States Plant Patent
Persson

(10) Patent No.: US PP11,995 P2
(45) Date of Patent: Jul. 17, 2001

(54) CHRYSANTHEMUM PLANT NAMED 'DARK PINK YOBLUSH'

(75) Inventor: Kjell Aake Persson, Trelleborg (SE)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/383,532

(22) Filed: Aug. 26, 1999

(51) Int. Cl.[7] ..... A01H 5/00
(52) U.S. Cl. ..... Plt./286
(58) Field of Search ..... Plt./286, 297

*Primary Examiner*—Howard J. Locker
(74) *Attorney, Agent, or Firm*—C. A. Whealy

(57) ABSTRACT

A distinct cultivar of Chrysanthemum plant named 'Dark Pink Yoblush', characterized by its upright, outwardly spreading and uniformly mounded plant habit; freely branching habit, full and dense plants; small, dark green leaves; uniform flowering; early flowering, eight-week response time; large daisy-type inflorescences that are about 11.7 cm in diameter; dark pink-colored ray florets; large disc with green disc florets that are slow to mature to bright yellow; and excellent postproduction longevity with inflorescences and leaves maintaining good substance and color for about four weeks in an interior environment.

2 Drawing Sheets

BACKGROUND OF THE INVENTION

The present invention relates to a new and distinct cultivar of Chrysanthemum plant, botanically known as *Dendranthema grandiflora* and hereinafter referred to by the cultivar name Dark Pink Yoblush.

The new Chrysanthemum was discovered by the Inventor in a controlled environment in Trelleborg, Sweden, as a naturally-occurring mutation of the *Dendranthema grandiflora* 'Pink Blush', disclosed in U.S. Plant Pat. No. 9,444. The new Chrysanthemum was observed as a single plant in a group of flowering plants of the parent cultivar. The selection of this plant was based on its different ray floret color. Compared to plants of the parent cultivar, Akron, plants of the new Chrysanthemum have much darker pink ray florets.

Asexual reproduction of the new Chrysanthemum by terminal cuttings harvested in a controlled environment in Alva, Fla., has shown that the unique features of this new Chrysanthemum are stable and reproduced true to type in successive generations.

SUMMARY OF THE INVENTION

The cultivar Dark Pink Yoblush has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Dark Pink Yoblush'. These characteristics in combination distinguish 'Dark Pink Yoblush' as a new and distinct Chrysanthemum:

1. Upright, outwardly spreading and uniformly mounded plant habit.

2. Freely branching habit, full and dense plants.

3. Small, dark green leaves.

4. Uniform flowering.

5. Early flowering, eight-week response time.

6. Can be produced as a disbudded or as a natural-spray type Chrysanthemum.

7. Large daisy-type inflorescenses that are about 11.7 cm in diameter when grown as a disbudded-type.

8. Dark pink-colored ray florets.

9. Large disc with green disc florets that are slow to mature to bright yellow.

10. Excellent postproduction longevity with inflorescences and leaves maintaining good substance and color for about four weeks in an interior environment.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type.

The photograph at the top of the first sheet comprises a top perspective view of a typical flowering plant of 'Dark Pink Yoblush'.

The photograph at the bottom of the first sheet comprises a close-up view of a typical inflorescence and upper (left) and lower (right) surfaces of typical leaves of the cultivar Dark Pink Yoblush.

The photograph at the top of the second sheet comprises a side perspective view of typical flowering plants of 'Dark Pink Yoblush' (left) and 'Pink Blush' (right).

The photograph at the bottom of the second sheet comprises a close-up view of typical inflorescences of plants of 'Dark Pink Yoblush' (left) and 'Pink Blush' (right). Floret and foliage colors in the photographs may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., and Leamington, Ontario, Canada, under greenhouse conditions which approximate those generally used in commercial potted Chrysanthemum production. Four unrooted cuttings were directly stuck in a 15-cm container and pinched once. Plants used for this description were grown as disbudded-types. Measurements and numerical values represent averages of typical flowering plants.

Botanical classification: *Dendranthema grandiflora* cultivar Dark Pink Yoblush.

Commercial classification: Daisy disbudded-type pot Chrysanthemum.

Parentage: Naturally-occurring mutation of *Dendranthema grandiflora* cultivar Pink Blush, disclosed in U.S. Plant Pat. No. 9,444.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Herbaceous daisy pot Chrysanthemum typically grown as a disbudded-type. Inverted triangle; compact; upright and outwardly spreading giving a uniformly mounded appearance to the plant. Freely branching; about four lateral branches develop after removal of terminal apex (pinching); dense and full plants.

*Plant height.*—About 24 cm.

*Plant width.*—About 37 cm.

*Stem texture.*—Pubescent.

*Stem color.*—146A.

*Foliage description.*—Arrangement: Alternate. Length: About 7.5 cm. Width: About 5.9 cm. Apex: Cuspidate. Base: Truncate to attenuate. Margin: Palmately lobed, sinuses between lateral lobes parallel to divergent. Texture: Upper and lower surfaces with very fine pubescence; veins prominent on lower surface. Petiole length: About 2.4 cm. Petiole diameter: About 3 mm. Color: Young foliage upper surface: Slightly darker than 147A. Young foliage lower surface: 147B. Mature foliage upper surface: Slightly darker than 147A. Mature foliage lower surface: 147B. Venation upper surface: 147A-147B. Venation lower surface: 147B.

Inflorescence description:

*Appearance.*—Daisy inflorescence form with oblong-shaped ray florets. Inflorescences borne on terminals above foliage, arising from leaf axils. Disk and ray florets arranged acropetally on a capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to three weeks of long day/short night conditions after planting followed by photoinductive short day/long night conditions flower about eight weeks later.

*Postproduction longevity.*—Inflorescences and leaves will maintain good color and substance for about four weeks in an interior environment.

*Quantity of Inflorescences.*—As a disbudded-type, all lateral inflorescences are removed to allow for maximum terminal inflorescence size. One inflorescense per lateral stem; about four inflorescences per plant.

*Inflorescence bud.*—Height: About 6 mm. Diameter: About 8 mm. Color: Greener than 143A.

*Inflorescence size.*—Diameter: About 11.7 cm. Depth (height): About 1.75 cm. Diameter of disc: Large, about 2.2 cm.

*Ray florets.*—Shape: Oblong. Orientation: Initially upright, then horizontal to peduncle. Aspect: Flat. Length: About 5.4 cm. Width: About 1.4 cm. Apex: Pointed to emarginate. Margin: Entire. Texture: Satiny. Number of ray florets per inflorescence: About 23. Color: When opening: 70B. Fully opened, upper surface: 70B to 75A overlaid with 70B. Fully opened, lower surface: Longitudinal stripes of 75B, 75C and 75D.

*Disc florets.*—Shape: Tubular. Apex: Serrated. Length: About 7.5 mm. Width: Apex, about 3.5 mm; base, about 1 mm. Number of disc florets per inflorescence: Numerous, about 122. Color: Immature: 144A. Mature: Apex: 9A. Mid-section: Light green. Base: White, 155D.

*Reproductive organs.*—Androecium: Present on disc florets only. Anther color: 9A. Pollen amount: Moderate to scarce. Pollen color: 14A. Gynoecium: Present on both ray and disc florets.

Disease resistance: Resistance to pathogens common to Chrysanthemums has not been observed on plants grown under commercial greenhouse conditions.

Seed production: Seed production has not been observed.

It is claimed:

1. A new and distinct cultivar of Chrysanthemum plant named 'Dark Pink Yoblush', as illustrated and described.

* * * * *

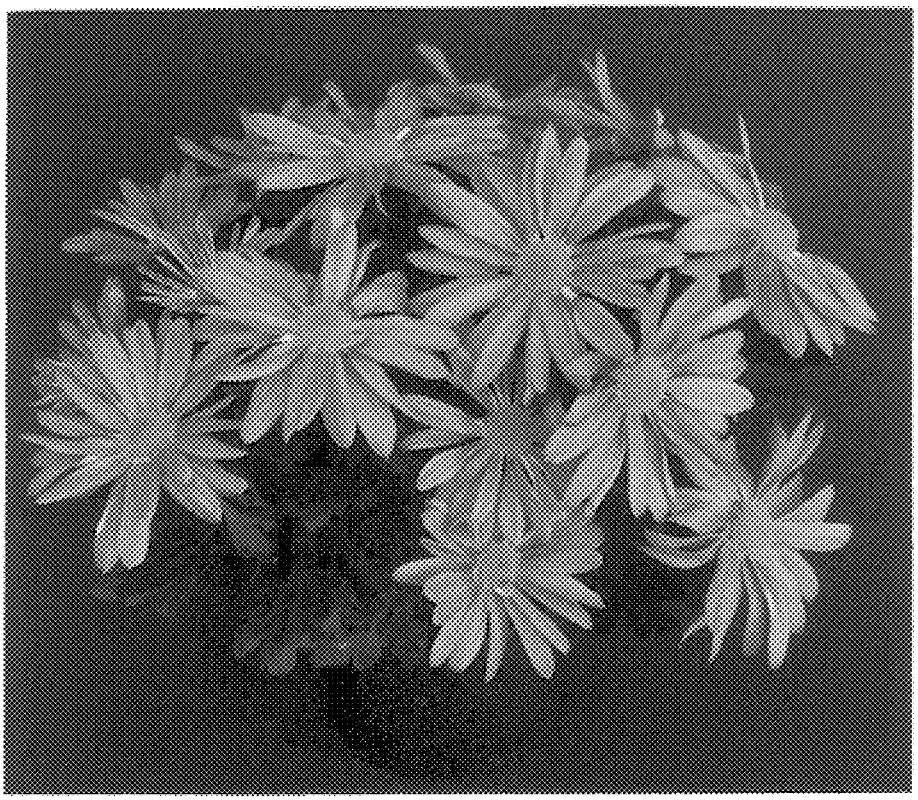
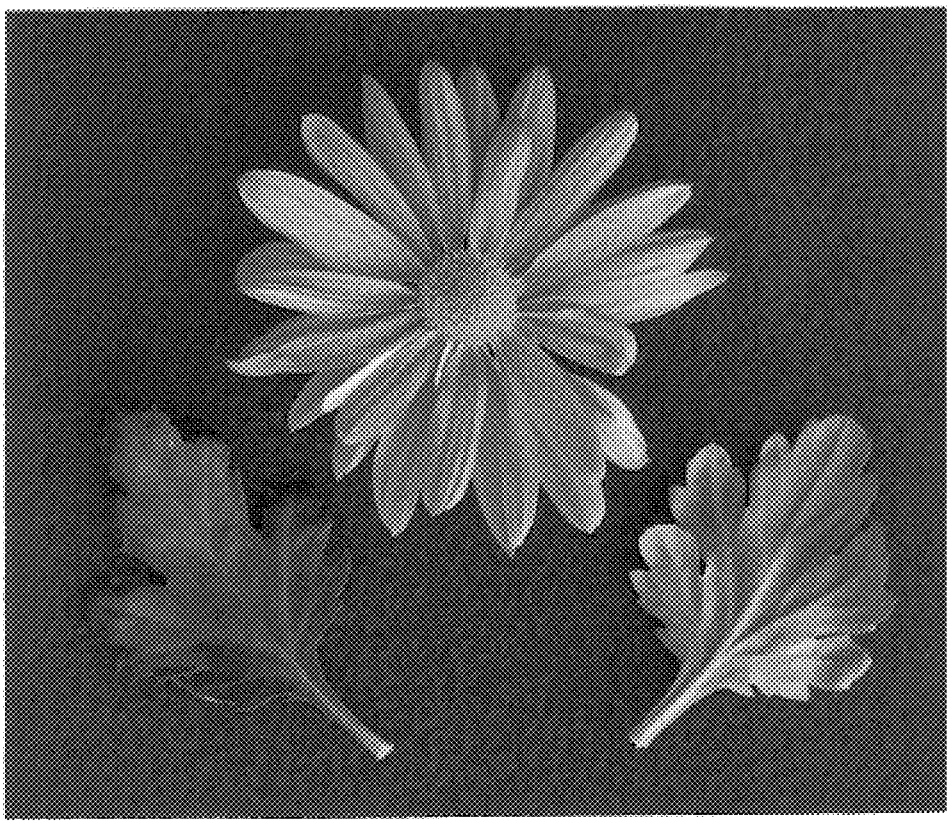

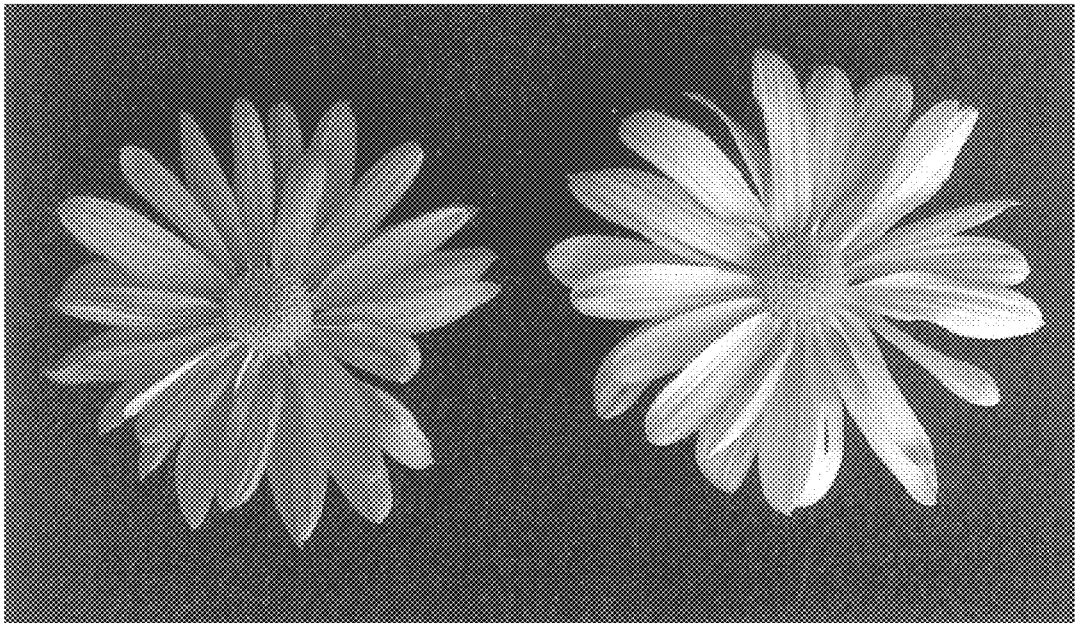

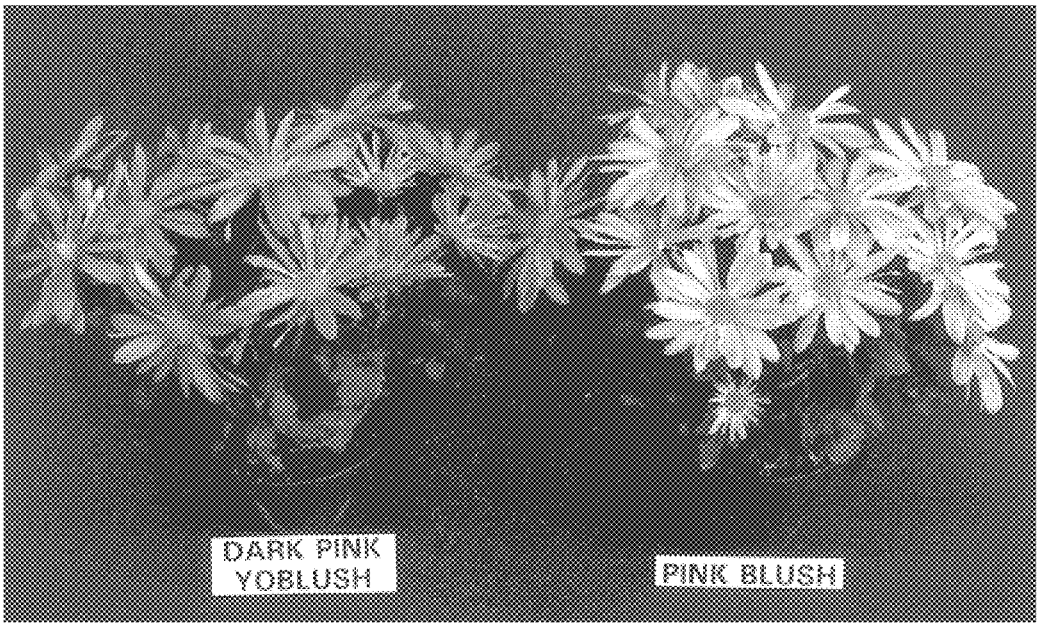
DARK PINK
YOBLUSH
PINK BLUSH